United States Patent [19]

Onwumere

[11] Patent Number: 5,159,050

[45] Date of Patent: Oct. 27, 1992

[54] POLYURETHANE AND MEDICAL ARTICLE THEREFROM

[75] Inventor: Fidelis C. Onwumere, Woodbury, Minn.

[73] Assignee: Becton, Dickinson and Company, Franklin Lakes, N.J.

[21] Appl. No.: 697,847

[22] Filed: May 9, 1991

[51] Int. Cl.$^5$ .................. C08G 18/70; C08G 37/10; A61K 31/725; A61K 31/765

[52] U.S. Cl. .................. 528/67; 424/78.08; 514/56; 536/21; 428/36.9; 428/364; 428/398

[58] Field of Search .............. 528/67; 424/78.08; 514/56; 536/21; 428/36.9, 364, 398

[56] References Cited

U.S. PATENT DOCUMENTS

| | | | |
|---|---|---|---|
| 3,634,123 | 1/1972 | Eriksson | 428/447 |
| 3,766,104 | 10/1973 | Bonin et al. | 528/80 |
| 3,810,781 | 5/1974 | Eriksson et al. | 424/423 |
| 3,969,301 | 7/1976 | Thurn | 528/67 |
| 4,024,871 | 5/1977 | Stephenson | 424/443 |
| 4,349,467 | 9/1982 | Williams et al. | 523/112 |
| 4,521,564 | 6/1985 | Solomon et al. | 523/112 |
| 4,613,517 | 9/1986 | Williams et al. | 424/78.18 |
| 4,865,870 | 9/1989 | Hu et al. | 427/2 |
| 4,873,308 | 10/1989 | Coury et al. | 528/75 |

OTHER PUBLICATIONS

*Biomaterials*, 218, 1983, Ferruti et al.
Azzuoli et al., *Biomaterials*, 8, 61, 1987.
Smith et al., *Anal. Biochem.*, 109, 466, 1980.
Brown, *Hematology Principles and Procedures*, Third Edition, Lea and Febiger Cp., 1980.
Chandler et al., *J. Biomedical Materials Research*, 22, 497, 1988.
Solomon et al., *J. Biomedical Materials Research*, 21, 43, 1987.

*Primary Examiner*—John Kight, III
*Assistant Examiner*—Rabon Sergent
*Attorney, Agent, or Firm*—Richard E. Brown

[57] ABSTRACT

A thermoplastic polyurethane has tertiary amino groups in the polymer chain. Protonation of the amino groups with an aqueous acid causes the polymer to absorb up to 1,000% by weight of water and swell. The protonated amino groups form a complex with an antithrombogenic agent to give an antithrombogenic polyurethane. The invention includes a shaped article of the polyurethane. The shaped article may be antithrombogenic.

20 Claims, No Drawings

POLYURETHANE AND MEDICAL ARTICLE THEREFROM

BACKGROUND OF THE INVENTION

1. Field of the Invention.

This invention relates to biomedical devices, and more specifically relates to a new polyurethane and an antithrombogenic medical device made therefrom.

2. Background of the Invention.

Extensive investigations have been undertaken over many years to find materials that will be biologically and chemically stable toward body fluids. This area of research has become increasingly important with the development of various objects and articles which can be in contact with blood or other body fluids, such as artificial organs, vascular grafts, probes, cannulas, catheters and the like.

Synthetic plastics have come to the fore as preferred materials for such articles. Polyurethanes in particular have many properties which make them attractive for fabrication of medical devices. They have excellent physical properties and are less thrombogenic than most other classes of polymers. Nevertheless, much effort has been directed to development of a truly nonthrombogenic polyurethane surface.

Thrombogenicity has conventionally been counteracted by the use of anticoagulants such as heparin. Various procedures for attachment of heparin to otherwise thrombogenic polymeric surfaces have been disclosed. Eriksson et al. in U.S. Pat. No. 3,634,123 discloses steeping a plastic surface sequentially in a solution of a cationic surface active agent and an aqueous solution of heparin to ionically bond the heparin. Improvements in the surface active agent-heparin coating method are described in U.S. Pat. No. 3,810,781 to Eriksson et al.

In U.S. Pat. Nos. 4,349,467 and 4,613,517 to Williams et al. and in U.S. Pat. No. 4,865,870 to Hu et al.

U.S. Pat. No. 4,521,564 to Solomon et al. discloses coating a polyurethane article with an amine-rich and covalently conjugating aldehyde-actuated heparin to the amino groups thereof.

In copending application Ser. No. 499,154 of common assignee herewith, a catheter made from a thermoplastic hydrophilic polyurethane having a polyethyleneoxide soft segment absorbs water and expands to a larger lumen size when contacted with an aqueous liquid and may include a bioactive agent and a radiopaque agent.

Ferruti et al. disclose the heparin binding capacity of crosslinked polyamidoamines prepared by reacting diamines with bis acryloylpiperazines (*Biomaterials*, 218 (1983)). Azzuoli et al. in Biomaterials 8, 61 (1987), disclose an antithrombogenic polyurethane graft copolymer. A polyurethane or polyurethaneurea base layer is coated with a diisocyante and the diisocyante coating reacted with the polyamidoamine of Ferruti supra. The grafted polyamidoamine is protonated and treated with a heparin salt.

While significant advances have been made toward antithrombogenic surfaces for fabrication of medical devices, further improvements are needed. In particular, materials having surfaces that are essentially nonthrombogenic for use in devices which will be in contact with blood for prolonged periods are needed. It is toward fulfillment of this need that this invention is directed.

SUMMARY OF THE INVENTION

A thermoplastic substantially hydrophobic polyurethane having latent hydrophilicity has tertiary amino groups in the polymer chain. Preferred polyurethanes include an aromatic diisocyanate, an alicyclic diisocyanate, and a diol chain extender in the hard segment. The soft segment includes a polyetherglycol and a hydroxy terminated polyurethane prepolymer. The prepolymer is preferably the reaction product of an aliphatic diisocyanate and a dihydroxy tertiary amine. The polyurethane is substantially hydrophobic, but when contacted with an aqueous acid, the amino groups are protonated and the polymer becomes hydrophilic, absorbs up to 1,000% by weight of water, and undergoes substantial swelling.

Another aspect of the invention is a polyurethane which is antithrombogenic, thermoplastic and hydrophilic. The antithrombogenic polyurethane is prepared by steeping the substantially hydrophobic polyurethane in a dilute aqueous mineral or organic acid solution containing an antithrombogenic agent, preferably heparin, whereby an ionic complex forms between the antithrombogenic agent and the protonated amino group.

The polyurethane, in either its hydrophobic or hydrophilic state, may be supplied as a shaped medical article, such as a swellable or nonswellable catheter. Preferred medical articles are antithrombogenic catheter tubings and obturator rods.

The polyurethane of this invention, when protonated, expands six to ten times more than swellable polyurethanes made with conventional hydrophilic soft segments such as polyethylene glycol, and the rate of water or saline uptake is much faster. The tertiary amine pendent groups along the polymer chain can be used to ionically attach bioactive agents, such as anti-infective/antithrombogenic agents or antibiotics without the use of conventional quaternary ammonium salt complexing agents. Unlike expandable polyurethanes formed from hydrophilic polyols, the polyurethane of this invention can be used in the unhydrated state as a nonswellable catheter or if desired, it can be hydrated and used as an expandable catheter.

The heparinized article of the invention does not include a coating of quaternary salt on a preformed device because the complexing agent is an integral part of the polymer chain. Thus, there is no danger of separation of quaternary salt into a patient's blood stream. Since quaternary salts are known to be hemolytic, an added margin of patient safety is provided by the present invention.

Release of heparin is almost undetectable after a few hours in contact with normal saline, yet the heparinized surface remains antithrombogenic after 24 hours. For patients on long term heparin therapy, this represents another safety factor because of the recently recognized and difficult to diagnose condition known as heparin induced thrombocytopenia.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In accordance with the invention, the new polyurethane is hydrophobic and has excellent physical properties making it useful for any application where water absorption is not desired. On the other hand, it has latent hydrophilicity so that the same material may be used for applications where it is desirable to combine its favorable mechanical properties with softness and swelling resulting from water absorption.

The polyurethane of the invention may be prepared, as described below, from three essential components. The first component of the new polyurethane is hereinafter called the isocyanate fraction. This fraction contains at least an aromatic diisocyanate and a nonaromatic diisocyanate. Suitable aromatic diisocyanate are toluene diisocyanate, 3,3'-diphenylmethane diisocyanate, 1,4 phenylenediisocyante, 2,2'-dimethyl 4,4'-biphenyldiisocyanate and 3,3'-dimethyl 4,4'-biphenyldiisocyanate. The preferred aromatic diisocyanate is 4,4'-diphenylmethanediisocyanate (MDI). methanediisocyanate (MDI).

The nonaromatic diisocyanate may be any aliphatic or alicyclic diisocyanate as known in the polyurethane art. Suitable nonaromatic diisocyanates have from about 4 to 18 carbon atoms branched or straight chain, such as 1,12-dodecanediisocyanate, 1,11-undecanediisocyanate, 1,10-decanediisocyanate, 1,9-nonanediisocyanate, 1,8-octanediisocyanate, 1,7-heptanediisocyanate, 1,6-hexanediisocyanate, 2,2,4-trimethyl-1,6-hexanediisocyanate, 1,4'-cyclohexanediisocyanate and preferably 4,4 dicyclohexylmethyldiisocyanate (HMDI). The disclosure will hereinafter be described in terms of the preferred MDI and HMDI. The ratio of MDI and HMDI in the isocyanate fraction may be about 35:65 to 65:35, preferably about 50:50 parts by weight.

The second component of the new polyurethane is a chain extender. Suitable chain extenders may be low molecular weight branched or unbranched diol, diamine or aminoalcohol of up to 10 carbon atoms, optionally fluorinated, or mixtures thereof. Representative nonlimiting examples of chain extenders are ethylene glycol; diethylene glycol; triethylene glycol; 1,2-propanediol; 1,3-propanediol; 1,6-hexanediol; 1,4-bis hydroxymethyl cyclohexane, hydroquinone dihydroxyethyl ether, ethanolamine, ethylenediamine bis hydroxyethylpiperazine and hexamethylenediamine. Preferred chain extenders are 1,6 hexanediol, ethylenediamine, hexamethylenediamine and most preferably, 1,4-butanediol (BDO).

The third component of the new polyurethane is a polyglycol fraction containing a polyether glycol and an amine containing hydroxy terminated polyurethane prepolymer.

Suitable polyetherglycols are substantially water insoluble hydrophobic glycols such as polypropyleneoxide glycol and preferably polytetramethyleneether glycol (PTMEG). For some applications, it may be desirable to use mixtures of polyetherglycols. These glycols may have a molecular weight of about 250 to 8,000. The most preferred polyether glycol is PTMEG of about 1,000 MW. This product is available from Dupont under the trade name Terathane ® T-1000.

The hydroxy terminated polyurethane prepolymer fraction of the polyglycol component may be the reaction product of about one mole of an aliphatic diisocyanate and about 2 moles of a bis (hydroxyalkyl) tertiary amine. Any aliphatic diisocyanate as described above for the isocyanate fraction may be used for synthesis of the prepolymer, preferably 1,6 hexane diisocyanate.

Bis (hydroxyalkyl) tertiary amines which may be used for prepolymer synthesis may have structure (1) below.

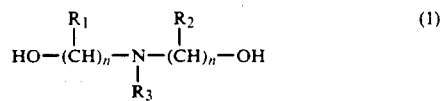

In structure (1), $R_1$ and $R_2$ may independently be hydrogen or lower alkyl, $R_3$ may be lower alkyl or dialkylaminoalkylene, and n may be 2 to 6. In structure (1), the term alkyl means about 1 to 18 carbon atoms and the term alkylene means about 2 to 6 carbon atoms. Suitable tertiary amines are, for example, N methyldiethanolamine, N propyldiethanol amine, N butyldiethanolamine, N dodecyldiethanolamine, N octadecyldiethanolamine, N ethyldiisopropanolamine and diethylaminopropyldipropanolamine. The preferred bis (hydroxyalkyl) tertiary amine is a dialkylamino alkyldialkanolamine, most preferably dimethylamino propyldiisopropanolamine, (DPA). This product is available from Texaco Chemical Co., Austin, Texas, under the trade name TEXACAT ®; and the invention will henceforth be described in terms of the preferred DPA.

The ratio of the polyether glycol and the prepolymer in the polyglycol fraction may be about 30/70 to 70/30 parts by weight. In the preferred polyurethane, the ratio is about 50/50 parts by weight.

The polyurethane of the invention may be synthesized by any conventional procedure as known in the polyurethane art. Preferably, a modification of the standard one shot method may be used. In the conventional one shot procedure, the isocyanate, polyglycol and extender components are mixed together with rapid stirring. In the present invention, the components of the prepolymer are mixed and stirred rapidly until the exotherm subsides and all isocyanate groups have reacted with hydroxyl groups. In this reaction, the tertiary amine groups of the DPA serve as a catalyst for the prepolymer formation. The isocyanate fraction, the chain extender and the polyether glycol may then be added. A mixture of these three components may be added, or, preferably, the extender and polyether glycol are added and mixed with the prepolymer, and the isocyanate fraction then added with vigorous stirring. Example I describes a typical synthetic procedure. As described above, the basic amino groups of the DPA catalyze the reaction of the isocyanate fraction with the hydroxyl groups of the prepolymer and extender.

The hard segment (HS) content of the new polyurethane may be about 40 to 70, preferably 45-60, most preferably about 50%. In this disclosure, the HS is calculated on the basis of the isocyanate fraction and extender and does not include the diisocyanate component of the prepolymer since this ingredient reacts only with the DPA and not with the extender. An isocyanate index of 1.0 to 1.1, preferably 1.02 may be used. From the desired HS content of the product and the molecular weights of the components, the proportions of the reagents to be used may readily be calculated.

If desired, the polyurethane may be crosslinked by inclusion in the formulation of a conventional polyurethane crosslinker, such as trimethanolpropane. The preferred polyurethane does not contain any crosslinkers and accordingly is fully thermoplastic and may be melt processed by extrusion or molding operations into any desired shape, such as rods, ribbons, tubings and sheets. Example II describes a typical melt processing experiment.

It has been found that the polyurethane of the invention is substantially hydrophobic, i.e., water absorption at equilibrium (after 6 hours soaking) is less than about 5%. These polymers have excellent mechanical properties and may find utility in a variety of applications for which water absorption is not useful.

On the other hand, if the polymer of the invention is hydrated in acidified water, it absorbs water up to 1,000% of its original weight. Hydration is accompanied by swelling and softening, and may be performed in any dilute acid, preferably, an organic acid. The most preferred acid for hydration may be dilute acetic acid of about 1 to 5, preferably 3% by volume. Hydration is substantially complete after 30 minutes at 50° C., 1 hour at 37° C. or about 8 hours at ambient temperature.

Advantage may be taken of the ability of the polyurethane to absorb water to prepare an anti-infective or antithrombogenic medical device. In this aspect of the invention, a medical device such as a rod to be used as an obturator or a tubing to be used as a catheter, may be melt processed into the desired shape and the shaped article steeped with acidified water, as described in Examples III and IV. The tertiary amino groups in the polyurethane chains are thereby protonated. When the amino groups are protonated, the hydrophobic polyurethane becomes hydrophilic and water absorption takes place. If the acidified water contains a bioactive agent capable of complexing with the protonated amine, a polyurethane having the bioactive agent complexed to the protonated nitrogen atom of the polymer chain is formed. No intermediate coating layer is required. Suitable bioactive agents are anti-infective agents, and anti-thrombogenic agents containing carboxylate and sulfonate groups capable of complexing with the protonated amine. Suitable anti infective agents are antibiotics such as penicillin and suitable antithrombogenic agents may be prostaglandins, urokinase, streptokinase tissue plasminogen activator and heparinoids. The preferred agent is heparin wherein protonation, hydration and heparinization are performed simultaneously by steeping the polyurethane in about a 0.05% by weight solution of sodium heparinate in 3% acetic acid. During the water absorption, the heparin is carried into the polyurethane so that the complexation of heparin occurs throughout the polymer matrix rather than just on the surface as in prior art methods. Example V describes the heparinization procedure.

The following examples are provided to further illustrate the invention but are not to be considered as limitative of the invention.

EXAMPLE I

A. Prepolymer Synthesis

A 5 liter glass reactor equipped with mechanical stirrer, thermometer and a nitrogen gas inlet was charged with 2.18 kg (10 moles) of TEXACAT® DPA. While stirring, 0.84 kg (5 moles) of hexamethylenediisocyanate was added to the reactor. Heat was not applied because the reaction was highly exothermic. The reaction was complete (disappearance of isocyanate by Infra Red) in about 4 hours.

B. Synthesis of 50% HS Polyurethane

Into a metal can was added 375 g of PTMEG, 375 g of the hydroxy-terminated prepolymer from A and 122 g of butanediol. With high speed air stirrer, the components were mixed thoroughly. To the can was added a mixture of 300 q of MDI and 314 of HMDI. The whole mixture was stirred for about 2 minutes or until an exotherm of 100° C was reached. The clear viscous melt was immediately poured into a teflon sheet and cured in an oven at 125° C for one hour.

Example I was repeated with the appropriate changes in component addition to give polyurethanes of 55 and 60% HS.

EXAMPLE II

Melt Processing

The polyurethanes from Example I were pelletized using a twin screw extruder, and the pellets then extruded into rods, ribbons and tubings using a 1 inch extruder.

EXAMPLE III

Polyurethane Water Absorption

Using a 50% HS polyurethane rod of 0.16 cm diameter, water absorption and increase of outside diameter (OD) were determined by steeping measured lengths of the rods in a 3% aqueous solution of acetic acid at 4° C. and withdrawing the rods periodically to measure weight differences and OD. The results obtained are given in Table I.

TABLE I

| INDWELLING TIME (min) | % WEIGHT INCREASE | % INCREASE IN O.D. |
|---|---|---|
| 5 | 50 | 17 |
| 10 | 100 | 32 |
| 25 | 167 | 62 |
| 45 | 267 | 98 |
| 60 | 333 | 109 |
| 120 | 650 | 149 |
| 240 | 983 | 174 |

EXAMPLE IV

Polyurethane Water Absorption; Effect of HS

The procedure of Example III was repeated using polyurethanes of 50, 55 and 60% HS. The results obtained are given in Table II:

TABLE II

| INDWELLING TIME (hrs) | PERCENT WEIGHT GAIN | | |
|---|---|---|---|
| | 50% HS | 55% HS | 60% HS |
| 1 | 333 | 170 | 40 |
| 2 | 650 | 340 | 60 |
| 3 | 820 | 480 | 80 |
| 4 | 983 | 550 | 100 |
| 5 | 1050 | 620 | 110 |
| 6 | 1050 | 620 | 110 |
| 7 | 1050 | 620 | 110 |

The hydrated 50% HS rod was then dehydrated in a forced air oven at 50° C for 1 hour, and the dehydrated rod then rehydrated in distilled water and normal saline by the procedure of Example III. After 1 hour, equilibrium weights were obtained and are expressed below as percentage increase in weight over original weights.

rehydration in water 176%
rehydration in normal saline 66%

This experiment showing hydration and dehydration of an extruded rod illustrates the preferred sequence of steps for fabrication of the catheter of the invention ready for rehydration and heparinization in 3% acetic acid.

EXAMPLE V

A. Heparinization of 50% HS rod

A heparin solution was made by dissolving 0.5 g of sodium heparinate in 100 ml of distilled water. To this solution was added 3 ml of glacial acetic acid. A polyurethane rod of about 125 sq cm was steeped in the acidified heparin solution at 40° C for 2 hours, then rinsed to remove occluded heparin solution from the rod surface.

The heparinized rod was then dehydrated by the procedure of Example IV and rehydrated by steeping in normal saline until an equilibrium weight was obtained. The results obtained are given in Table III:

TABLE III

| INDWELLING TIME (min) | WEIGHT GAIN (%) | INCREASE IN O.D. % |
|---|---|---|
| 5 | 39 | 4.5 |
| 10 | 48 | 4.5 |
| 25 | 79 | 13.6 |
| 45 | 79 | 13.6 |
| 60 | 100 | 23 |
| 120 | 100 | 23 |
| 240 | 100 | 23 |

B. Heparinization of 60% HS

The 60% HS rod of Example IV, after hydration and dehydration, was heparinized as described above in A. Although this rod took up much less water, it complexed the same quantity of heparin, showing that the 0.05% heparin in 3% acetic acid solution permeated the entire bulk of the 60% HS rod.

EXAMPLE VI

Antithrombogenicity In vitro

The heparin ionically bound to the polyurethane rods was determined by three test protocols after rinsing the heparinized rods for 4, 8 and 24 hrs in normal saline. Release rates and total extractable heparin were assayed colorimetrically using toluidine blue by the procedure of P. K. Smith, et al., *Anal. Biochem.*, 109, 466 (1973). *In vitro* heparin activity was determined by the partial thromboplastin time (P.T.T., a measure of the clotting time) as described by B. A. Brown, *Hematology Principles and Procedures*, Third Edition, Lea and Febiger Co. 1980. Heparin activity on the surface of the rod was determined using the Thrombin Inactivation Assay, (Chandler et al , *J. Biomedical Materials Research*, 22, 497 (1988).

The results of these experiments are given in Table IV:

TABLE IV

| TOTAL HEPARIN QUANTITY EXTRACTED 201 ug/cm² | | | |
|---|---|---|---|
| TIME (hrs) | RELEASE RATE (ug/cm²/min) | P.T.T. (secs) | SURFACE ACTIVITY (units/cm²) |
| 4 | 0.0004 | >1800 | 0.03 |
| 8 | <test range | >1800 | 0.04 |
| 24 | <test range | >1800 | 0.03 |

The P.T.T. and surface activity tests demonstrate that heparin activity is still present long after the release rate study shows that heparin release is complete.

EXAMPLE VII

Antithrombogenicity In vivo

In vivo antithrombogenic response of the heparinized rod was measured by gamma camera scintigraphy (Solomon et al., *J. Biomedical Materials Research* 21, 43 (1987).

A commercially available nonheparinized control polyurethane rod was inserted into one jugular vein of a dog and the heparinized 50% HS rod of Example V was inserted into the other jugular vein of the same animal (in order to neutralize dog to dog variation). Platelet adhesion and thrombus deposition were determined from the average platelet uptake slope and thrombus weight from three dogs.

The results of this experiment are given in Table V.

TABLE V

| SCINTIGRAPHY RESULTS 40 MINUTE PLATELET RESPONSE | | | |
|---|---|---|---|
| MATERIAL | NUMBER OF SCANS | AVERAGE SLOPE | AVERAGE THROMBUS WEIGHT |
| Control Polyurethane Nonheparinized | 6 | 0.13 ± 0.007 | 80.5 ± 36.0 mg |
| Example I Polyurethane Nonheparinized | 2 | 0.10 ± 0.005 | 220 ± 11.0 mg |
| Example I Polyurethane Heparinized. 4 hr rinse | 2 | 0.01 ± 0.002 | 1.0 ± 0.0 mg |
| Example I Polyurethane Heparinized 24 hr rinse | 2 | 0.04 ± 0.004 | 0.0 ± 0.0 mg |

It is seen that the heparinized polyurethane rod of the invention gives substantially no thrombus after 24 hour rinse, even though the results of the toluidine blue test shows a release rate below the sensitivity of the test.

It is believed, although not substantiated, that the heparin binding to the surface of the rod is sufficiently strong to prevent release of the heparin, and that the data indicates that heparin release is not essential for antithrombogenicity.

What is claimed is:

1. A thermoplastic substantially hydrophobic polyurethane comprising the reaction product of an isocyanate fraction, a diol chain extender and a polyglycol fraction, said isocyanate fraction comprising an aromatic diisocyanate and an alicyclic diisocyanate, said polyglycol fraction comprising polytetramethyleneether glycol and a hydroxy terminated prepolymer, said prepolymer comprising the reaction product of an aliphatic diisocyanate and a dialkylaminoalkyldialkanolamine.

2. The polyurethane of claim 1 wherein said aromatic diisocyanate is selected from the group consisting of toluene diisocyanate, 4,4'-diphenylthanediisocyanate, 1,4 phenylenediisocyanate, 2,2'-dimethyl-4,4'-biphenyldiisocyanate and 3,3'-dimethyl-4,4'-biphenyldiisocyanate.

3. The polyurethane of claim 1 wherein said alicyclic diisocyanate is selected from the group consisting of isophorone diisocyanate, 1,4-cyclohexanediisocyanate and 4,4'-dicyclohexylmethanediisocyanate.

4. The polyurethane of claim 1 wherein said chain extender is selected from the group consisting of ethylene glycol; diethylene glycol; triethylene glycol; 1,2 propanediol; 1,3-propanediol; 1,6 hexanediol; 1,4-hydroxymethyl cyclohexane, hydroquinone dihydroxyethyl ether, and 1,4 butanediol.

5. The polyurethane of claim 1 wherein said aliphatic diisocyanate has about 4 to 18 carbon atoms.

6. The polyurethane of claim 1 wherein said dialkylaminoalkyldialkanolamine is selected from the group consisting of diethylaminopropyldipropanolamine and dimethylaminopropyldiisopropanolamine.

7. A thermoplastic substantially hydrophobic polyurethane comprising the reaction product of an isocyanate fraction, a chain extender, and a polyglycol fraction, said isocyanate fraction comprising a mixture of an aromatic diisocyanate and a nonaromatic diisocyanate, said polyglycol fraction comprising a polyetherglycol and a hydroxy terminated prepolymer, said prepolymer comprising the reaction product of an aliphatic diisocyanate and a bis(hydroxyalkyl) tertiary amine.

8. The polyurethane of claim 7 wherein said bis hydroxyalkyl tertiary amine is selected from the group having the formula

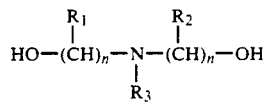

wherein $R_1$ and $R_2$ are independently hydrogen or lower alkyl, $R_3$ is selected from the group consisting of lower alkyl or dialkylaminoalkylene, n is 2 to 6, alkyl is 1 to about 18 carbon atoms and alkylene is 2 to about 6 carbons atoms.

9. A thermoplastic substantially hydrophobic polyurethane comprising the reaction product of an isocyanate fraction, 1,4-butanediol and a polyglycol fraction, said isocyanate fraction comprising 4,4'-diphenylmethanediisocyanate and 4,4'-dicyclohexylmethanediisocyanate, said polyglycol fraction consisting essentially of polytetramethyleneether glycol and a hydroxy terminated prepolymer, said prepolymer comprising the reaction product of hexamethylenediisocyanate and N-dimethylaminopropyldiisopropanolamine.

10. An antithrombogenic polyurethane comprising the reaction product of an isocyanate fraction, a diol chain extender and a polyglycol fraction, said isocyanate fraction comprising an aromatic diisocyanate and an alicyclic diisocyanate, said polyglycol fraction comprising polytetramethyleneether glycol and a hydroxy terminated prepolymer, said prepolymer comprising the reaction product of an aliphatic diisocyanate and a dialkylaminoalkyldialkanolamine, said amine being protonated and complexed with heparin.

11. The polyurethane of claim 10 wherein said aromatic diisocyanate is selected from the group consisting of toluene diisocyanate, 4,4'-diphenyl methanediisocyanate, 3,3'-diphenylmethanediisocyanate, 1,4 phenylenediisocyanate, 2,2'-dimethyl-4,4'-biphenyldiisocyanate and 3,3'-dimethyl 4,4'-biphenylphenyldiisocyanate.

12. The polyurethane of claim 10 wherein said alicyclic diisocyanate is selected from the group consisting of isophorone diisocyanate, 1,4-cyclohexanediisocyanate and 4,4'-dicyclohexylmethanediisocyanate.

13. The polyurethane of claim 10 wherein said chain extender is selected from the group consisting of ethylene glycol; diethylene glycol; triethylene glycol; 1,2 propanediol; 1,3 propanediol; 1,6-hexanediol; 1,4 hydroxymethyl cyclohexane, hydroquinone dihydroxyethyl ether, and 1,4-butanediol.

14. The polyurethane of claim 10 wherein said aliphatic diisocyanate has about 4 to 18 carbon atoms.

15. The polyurethane of claim 10 wherein said dialkylaminoalkyldialkanolamine is selected from the group consisting of diethylaminopropyldipropanolamine and dimethylaminopropyldiisopropanolamine.

16. The polyurethane of claim 10 in the form of a rod.

17. The polyurethane of claim 10 in the form of a tubing.

18. A bioactive polyurethane comprising the reaction product of an isocyanate fraction, a chain extender, and a polyglycol fraction, said isocyanate fraction comprising a mixture of an aromatic diisocyanate and a nonaromatic diisocyanate, said polyglycol fraction comprising a polyetherglycol and a hydroxy terminated prepolymer, said prepolymer comprising the reaction product of an aliphatic diisocyanate and a bis(hydroxyalkyl) tertiary amine, said amine being protonated and complexed with a heparin.

19. The polyurethane of claim 18 wherein said bis (hydroxyalkyl) tertiary amine is selected from the group having the formula

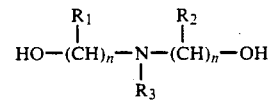

wherein $R_1$ and $R_2$ are independently hydrogen or lower alkyl, $R_3$ is selected from the group consisting of lower alkyl or dialkylaminoalkylene, n is 2 to 6, alkyl is 1 to about 18 carbon atoms and alkylene is 2 to about 6 carbons atoms.

20. An antithrombogenic polyurethane comprising the reaction product of an isocyanate fraction, 1,4 butanediol and a polyglycol fraction, said isocyanate fraction comprising 4,4'-diphenylmethanediisocyanate and 4,4'-dicyclohexylmethanediisocyanate, said polyglycol fraction consisting essentially of polytetramethyleneether glycol and a hydroxy-terminated prepolymer, said prepolymer comprising the reaction product of hexamethylene diisocyanate and N-dimethylaminopropyl diisopropanolamine, said amine being protonated and complexed with heparin.

* * * * *